United States Patent [19]

Orgain et al.

[11] Patent Number: 5,575,648
[45] Date of Patent: Nov. 19, 1996

[54] DENTAL TURBINE SPINDLE ASSEMBLY

[75] Inventors: Jason E. Orgain; Robert Larsen, both of Chico, Calif.

[73] Assignee: Lares Research, Inc., Chico, Calif.

[21] Appl. No.: 404,143

[22] Filed: Mar. 13, 1995

[51] Int. Cl.⁶ .................................................. A61C 1/14
[52] U.S. Cl. ............................................ 433/127; 433/132
[58] Field of Search ........................... 433/127, 128, 433/129, 132; 279/36, 42, 43.3, 43.4, 48, 52, 56, 59

[56] References Cited

U.S. PATENT DOCUMENTS 4,198,754  4/1980  Lares et al. ............................. 433/129
4,318,695  3/1982  Lieb et al. ............................. 433/132

*Primary Examiner*—Cary E. O'Connor
*Attorney, Agent, or Firm*—John P. O'Banion

[57] ABSTRACT

A high speed dental handpiece turbine spindle assembly in which a generally cylindrical spindle is rotatably mounted within a housing for actuation by a supply of pressurized air acting upon turbine blades associated with the spindle. The spindle includes a longitudinal bore which accommodates a drill bit or bur, with one end of the spindle being tapered and threaded to fit a matching chuck nut. The spindle and chuck nut have interfering geometry so that the chuck nut cannot be inadvertently removed while changing drill bits, and so that the chuck nut cannot be inadvertently tightened so far that the spindle is permanently deformed.

4 Claims, 1 Drawing Sheet

DENTAL TURBINE SPINDLE ASSEMBLY

BACKGROUND OF THE INVENTION

1. Field of the Invention

This invention pertains to dental handpieces generally, and more particularly to a turbine spindle assembly in which the loosened chuck nut is retained and does not experience undesired movement during changing of burs or drill bits.

2. Description of the Background Art

Dental handpieces for supporting drills and burs generally comprise multi-component arrangements wherein a turbine rotor or spindle is driven by compressed air or mechanical means. The turbine or spindle imparts rotational motion to the drill bit or bur. Currently available dental handpieces generally have means for holding a drill bit or bur in the handpiece in the form of a chuck nut and threaded spindle assembly. For example, U.S. Pat. No. 4,198,754, incorporated herein by reference, discloses a dental turbine spindle assembly in which a spindle with turbine rotors is rotatably mounted within a housing, and drill bits and burs are interchangeably attached by inserting in a bore within the spindle, and tightening or loosening a chuck nut which threads onto the spindle. A common problem, however, is that when the chuck nut is loosened from the spindle member in order to withdraw one bit and insert another, the loosened chuck nut can slip off the threaded portion of the spindle altogether, resulting in unwanted delay while the nut is recovered. Another problem is that accidental tightening of the chuck when a drill bit or bur is not engaged in the spindle can result in permanent damage to the threaded end of the spindle, rendering it unusable. Since the spindles are high-precision parts machined for spinning at high speeds, replacement is generally expensive.

As can be seen therefore, there is a need for a turbine or spindle assembly for a dental handpiece wherein the loosened chuck nut is physically retained on the spindle, and wherein accidental permanent deformation of the spindle is prevented when the chuck nut is tightened. The present invention satisfies these needs, as well as others, and overcomes the deficiencies found in currently available dental handpieces.

SUMMARY OF THE INVENTION

The present invention pertains to means for retaining a loosened chuck nut and for preventing deformation of a threaded spindle by inadvertent tightening of the chuck nut in a dental handpiece or attachment. In general terms, a handpiece in accordance with the present invention includes a generally cylindrical spindle or turbine rotatably mounted within a housing, and means for rotatably actuating the spindle or turbine. A plurality of bearings within the housing reduce friction so the spindle may rotate at high speed. The spindle contains a longitudinal bore which accommodates a drill bit or bur, with one end of the spindle tapered and threaded to fit a matching chuck nut. Chuck nut retaining means and spindle deformation preventing means are provided in the form of a spindle and chuck nut which have interfering geometries, so that the chuck nut cannot be inadvertently removed while changing drill bits, and so that the chuck nut cannot be inadvertently tightened so far that the spindle is permanently deformed or damaged.

By way of example and not of limitation, the present invention includes an encircling flange adjacent to the threaded portion of the spindle, and a circumferential groove adjacent to the flange. The chuck nut includes a skirt, the skirt having a circumferential, inwardly disposed lip structured and configured to fit loosely within the circumferential groove on the spindle. An anti-friction bearing covers or houses the chuck nut skirt, thereby preventing flaring of the skirt when unthreaded. When the chuck nut is unthreaded on the spindle to loosen and change drill bits, the lip on the chuck nut moves within the groove in the spindle until it comes to rest against the flange and is prevented from overcoming the spindle groove by contact with part of the anti-friction bearing, thus preventing further unthreading movement and retaining the chuck nut on the spindle. When the chuck nut is tightened by threading, the lip on the chuck nut moves within the groove until it comes to rest against the main body of the spindle adjacent to the groove, preventing further tightening which may damage the spindle.

An object of the present invention is to provide a turbine spindle assembly for a dental handpiece in which the loosened chuck nut is retained on the spindle.

Another object of the invention is to provide a turbine spindle assembly for a dental handpiece which prevents the chuck nut from being tightened on the spindle in a manner which causes deformation to the spindle.

Further objects and advantages of the invention will be brought out in the following portions of the specification, wherein the detailed description is for the purpose of fully disclosing the preferred embodiments of the invention without placing limits thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Figure 1:
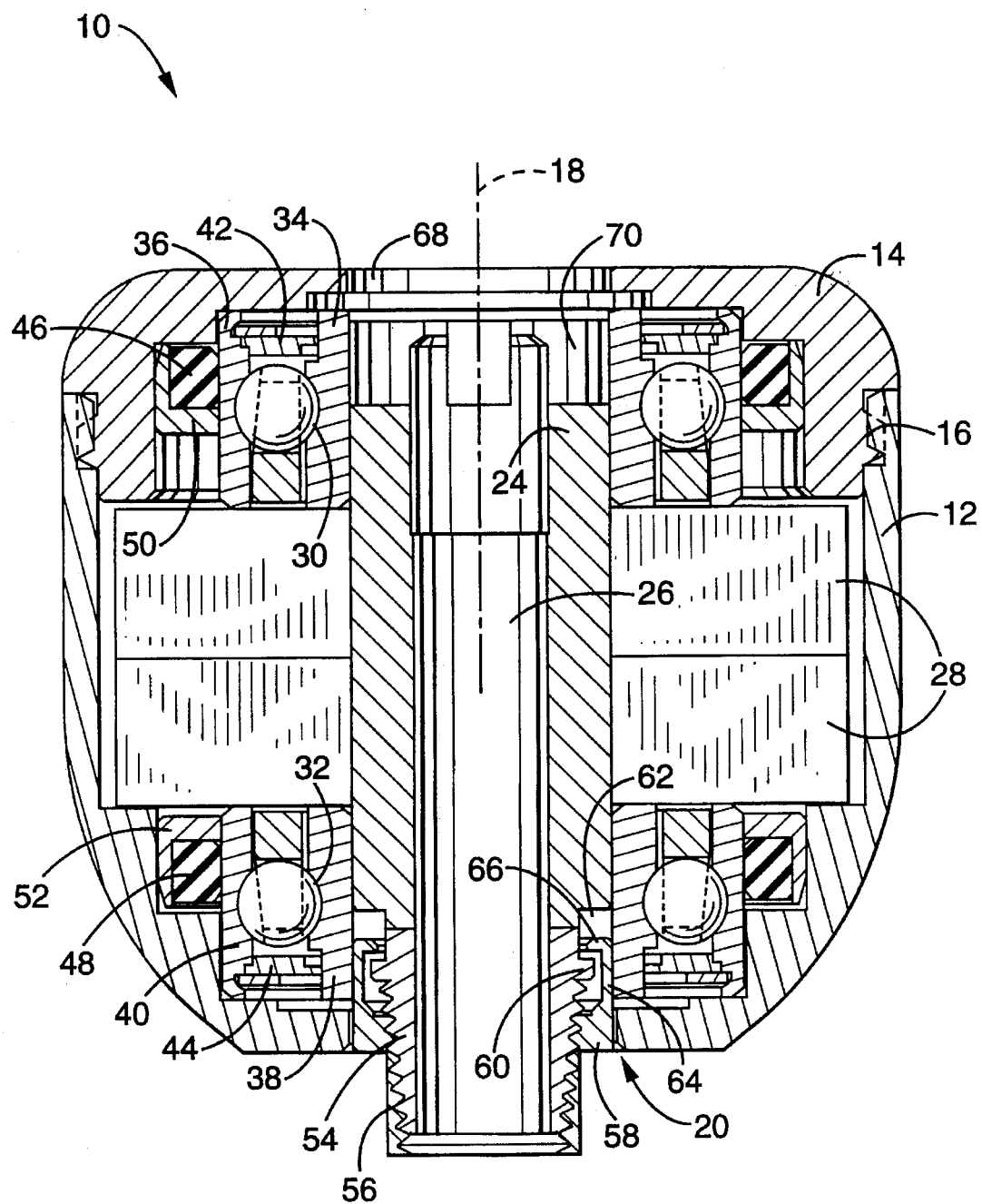
FIG. 1 is section view of a turbine spindle assembly in accordance with the present invention.

Referring more specifically to the drawings, for illustrative purposes the present invention is embodied in the apparatus generally shown in FIG. 1. It will be appreciated that the apparatus may vary as to configuration and as to details of the parts without departing from the basic concepts as disclosed herein.

Referring to FIG. 1, a turbine spindle assembly 10 is shown which includes a housing 12 and a cap member 14 that reversibly engages housing 12, preferably by threads 16 or other conventional fastening means. Housing 12 has a longitudinal axis 18 with an opening 20 along axis 18.

A generally cylindrical spindle or turbine 24 is rotatably mounted in housing 12 along axis 18. Spindle 24 includes a longitudinal bore 26 which is structured and configured to reversibly engage dental tools such as burs and drill bits. Means for rotatably actuating the spindle 24 are included in the invention, and is shown in FIG. 1 as a plurality of air-driven turbine blades 28 are located axially about spindle 24. It is also contemplated that the actuating means may comprise a geared or mechanical drive arrangement instead of blades 28.

A plurality of bearings which, in the preferred embodiment are shown as upper and lower bearings 30, 32, are included in housing 12 adjacent spindle 24 to allow rotation of spindle 24. Bearing 30 includes inner bearing race 34 and outer bearing race 36, while bearing 32 includes inner bearing race 38 and outer bearing races 40. Shields 42, 44 are also included with bearings 30, 32, respectively. Bearing supports, preferably in the form of elastomeric rings 46, 48 provide support for bearings 30, 32. Retainers 50, 52 hold rings 46, 48 in place. As shown, spindle 24 is positioned for optimum balance and only partly engages inner races 34, 38. Turbine blades 28 are positioned between bearings 30, 32. Turbine blades 28 are generally driven by compressed air means in the form of a high pressure air inlet, air line, and exhaust outlet (not shown). As related above, a geared or mechanical drive means for transmitting rotational motion to spindle 24 are also contemplated for use with the present invention.

Spindle 24 includes a tapered end portion 54 having external threads 56. As shown, end portion 54 protrudes from housing 12 through opening 20. Preferably, spindle end portion 54 is an integral part of spindle 24, and is shaped by precision machining. It is contemplated however, that end portion 54 could be fabricated separately and attached to spindle 24 by suitable means such as threading. A chuck nut 58 engages threads 56 on end portion 54.

Means for retaining chuck nut 58 on spindle 24, and means for preventing permanent deformation of spindle 24 are provided in the present invention, preferably in the form of interfering geometries for spindle 24 or end portion 54 and chuck nut 58. In the preferred embodiment, the retaining and preventing means include an encircling flange 60 on end portion 54 adjacent to threads 56, and a circumferential groove 62 on spindle 24 located adjacent to flange 60. Groove 62 generally marks the boundary between the main body of spindle 24 and the tapered end portion 54. A plurality of thin longitudinal slots (not shown) located axially on spindle end portion 54 divide end portion 54 into a plurality of jaws (not shown).

Chuck nut 58 includes internal threads as shown which mate with and reversibly engage external threads 56 of spindle end portion 54. The chuck nut retaining means and spindle deformation preventing means further includes a circular skirt 64 on chuck nut 58, with skirt 64 including a circumferential, inwardly disposed lip 66. Lip 66 is generally structured and configured to fit loosely within groove 62 on spindle end portion 54, between flange 60 and the main body of spindle 24. Chuck nut 58 generally includes suitable external features (not shown) to allow reversible engagement with a wrench or other tool used for tightening and loosening.

Other interfering geometric arrangements of chuck nut 58 and spindle end portion 54 are also possible as chuck nut retaining means and spindle deformation preventing means. For example, end portion 54 or spindle 24 could include an annular flange which interferingly engages an inward facing groove in skirt 64 on chuck nut 58. Additional interfering geometrical arrangements of these components are also possible, and are considered to be within the scope of the present invention.

If desired, an opening 68 may be included in cap member 14, so that a tool can be inserted into housing to aid in securing burs or drill bits. As shown, spindle 24 includes slots 70 adjacent opening 68, with slots 70 structured and configured to engaged suitable tools, such as screwdrivers, wrenches, and the like.

The subject invention is used by engaging a dental tool (not shown) such as a drill bit or bur, in longitudinal bore 26 of spindle 24 while chuck nut 58 is loosened on threads 56 of spindle end portion 54. Tightening of chuck nut 58 on threads 56 causes the jaws (not shown) of end portion 54 to constrict about the dental tool, thus frictionally engaging the dental tool in bore 26, and allowing use of the tool for procedures at high rotational speeds. Loosening chuck nut 58 on threads 56 of spindle end portion 54 causes the jaws to relax, permitting the dental tool to be disengaged from bore 26 and allowing substitution of a different tool.

When chuck nut 58 is loosened from threads 56 on spindle end portion 54, lip 66 on skirt 64 moves within groove 62 towards flange 60, until lip 66 comes to rest against flange 60, preventing further loosening by unthreading. Chuck nut 58 thus cannot be completely unthreaded and separated from spindle end portion 54, and is retained on end portion 54. This retention of loosened chuck nut 58 on spindle end portion 54 eliminates the danger of losing chuck nut 58, which is generally of small dimensions and easily misplaced. The danger of contamination of chuck nut 58 due to accidental disengagement from the spindle 24 and end portion 54, which may require sterilization, is also eliminated.

As chuck nut 54 is tightened on threads 56, lip 66 moves within groove 62 away from flange 60 until it comes to rest against the main body of spindle 24, preventing further tightening on spindle end portion 54. Since, as aforementioned, when chuck nut 58 is tightened on threads 56, the jaws of the end portion 54 constrict, and if a dental tool is not present in bore 26, this constriction of the jaws can proceed so far as to become permanent. The deformation of the spindle end portion 54 resulting by permanent constriction of the jaws prevents insertion of dental tools even when the chuck nut 58 is loosened again, and generally required replacement of the spindle 24. Thus, the dimensions of skirt 64 and geometry of lip 66 and groove 62 are structured and configured so that lip 66, upon tightening chuck nut 58 on threads 56, comes into contact with the main body of spindle 24 before permanent deformation of the end portion 58 occurs. The structure and configuration of skirt 64, lip 66, and groove 62, however, is such that adequate tightening of chuck nut 58 is allowed to securely and properly engage dental tools within bore 26.

Accordingly, it will be seen that this invention provides a spindle assembly for a dental hand piece which retains the chuck nut on the spindle, and which prevents the chuck nut from deforming the spindle due to over-tightening. Although the description above contains many specificities, these should not be construed as limiting scope of the invention but as merely providing illustrations of some of the presently preferred embodiments of this invention. Thus, the scope of this invention should be determined by the appended claims and their legal equivalents.

What is claimed is:

1. A dental handpiece spindle assembly, comprising:
    (a) a housing, said housing having a longitudinal axis, said housing including an opening along said axis;
    (b) a cylindrical spindle rotatably mounted in said housing along said axis, said spindle including a longitudinal bore;
    (c) said spindle including a tapered end portion, said end portion including external threads;
    (d) means for rotatably actuating said spindle;
    (e) a chuck nut, said chuck nut including internal threading;
    (f) a circular skirt associated with said chuck nut, said skirt having a circumferential, inwardly disposed lip; and
    (g) retaining means associated with said chuck nut and said spindle for retaining said chuck nut on said spindle when said chuck nut is loosened and preventing permanent deformation of said spindle when said chuck nut is tightened.

2. A dental handpiece spindle assembly as recited in claim 1, wherein said retaining means comprises:

(a) an encircling flange adjacent said external threads of said end portion of said spindle; and (b) a circumferential groove adjacent said flange.

3. A spindle assembly for a dental handpiece, comprising:

(a) a housing, said housing having a longitudinal axis, said housing including an opening along said axis;

(b) a cylindrical spindle rotatably mourned in said housing along said axis, said spindle including a longitudinal bore;

(c) said spindle including a tapered end portion, said end portion including external threads, said end portion including an encircling flange adjacent said external threads, said end portion including a circumferential groove adjacent said flange, said end portion projecting from said opening in said housing;

(d) means for rotatably actuating said spindle; and (e) a chuck nut, said chuck nut including internal threads, said chuck nut including a circular skirt, said skirt having a circumferential, inwardly disposed lip.

4. A dental handpiece turbine, comprising:

(a) a housing, said housing having a longitudinal axis, said housing including an opening along said axis, said housing including a reversibly engageable cap, said cap having an opening;

(b) a plurality of bearings included in said housing about said axis, said bearings including elastomeric bearing supports, said bearing supports including retainers, said bearings including races;

(c) a cylindrical spindle rotatably mounted in said housing along said axis, said spindle including a longitudinal bore, said spindle partially engaging each of said bearings, said spindle having first and second ends;

(d) a tapered end portion included on said first end of said spindle, said end portion including external threads, said end portion including an encircling flange adjacent said external threads, said end portion including a circumferential groove adjacent said flange, said end portion projecting from said opening in said housing;

(e) a plurality of turbine blades, said turbine blades axially coupled to said spindle, said turbine blades located between said bearings; and (f) a chuck nut, said chuck nut including internal threading, said chuck nut including a circular skirt, said skirt having a circumferential, inwardly disposed lip.

* * * * *